United States Patent
Pratte et al.

(10) Patent No.: US 8,511,510 B2
(45) Date of Patent: Aug. 20, 2013

(54) SYSTEM AND METHOD FOR MEDICAL INSTRUMENT STERILIZATION CASE HAVING A ROTATABLY DISPLACING COVER

(75) Inventors: David R. Pratte, Manchester, NH (US); Michael Sullivan, Manchester, NH (US)

(73) Assignee: Symmetry Medical Manufacturing, Inc., Warsaw, IN (US)

( * ) Notice: Subject to any disclaimer, the term of this patent is extended or adjusted under 35 U.S.C. 154(b) by 360 days.

(21) Appl. No.: 12/753,500

(22) Filed: Apr. 2, 2010

(65) Prior Publication Data
US 2010/0252468 A1   Oct. 7, 2010

Related U.S. Application Data

(60) Provisional application No. 61/166,348, filed on Apr. 3, 2009.

(51) Int. Cl.
*B65D 43/16* (2006.01)

(52) U.S. Cl.
USPC ............ 220/812; 206/752; 16/359; 16/361

(58) Field of Classification Search
USPC ............ 206/439, 363, 438, 759, 45.23; 220/811–816; 49/260; 16/348, 357, 358, 16/359, 360, 361, 345
See application file for complete search history.

(56) References Cited

U.S. PATENT DOCUMENTS

| 391,145 | A | * | 10/1888 | Hardin | 229/125.11 |
|---|---|---|---|---|---|
| 2,112,451 | A | * | 3/1938 | Best et al. | 206/506 |
| 4,420,079 | A | * | 12/1983 | Gliniorz et al. | 206/408 |
| 4,685,567 | A | * | 8/1987 | Webb | 206/506 |
| 5,411,134 | A | * | 5/1995 | Temple et al. | 206/753 |
| 5,520,313 | A | * | 5/1996 | Toshihide | 224/539 |
| 6,116,452 | A | * | 9/2000 | Hamel et al. | 220/318 |
| 6,470,627 | B2 | * | 10/2002 | Fukuo | 49/260 |
| 6,478,160 | B1 | * | 11/2002 | Au et al. | 206/752 |
| 6,669,023 | B2 | * | 12/2003 | Kikuchi et al. | 206/759 |
| 2001/0052524 | A1 | * | 12/2001 | Ichimaru et al. | 220/815 |

FOREIGN PATENT DOCUMENTS

| JP | 05042190 U | 6/1993 |
|---|---|---|
| JP | 03032007 U9 | 9/1996 |
| JP | 09226799 A | 9/1997 |
| JP | 09285331 A | 11/1997 |
| JP | 2000159251 A | 6/2000 |
| JP | 2002166952 A | 6/2002 |
| JP | 2003026160 A | 1/2003 |

* cited by examiner

*Primary Examiner* — Andrew Perreault
(74) *Attorney, Agent, or Firm* — Hayes Soloway PC (57) ABSTRACT

A medical instrument sterilization container has a plurality of walls and a rotatably displacing cover. A rotatable device is integral with the cover. An elongate slot is formed in a side of the container for receiving the rotatable device. The rotatable device is slidable within the elongate slot.

18 Claims, 10 Drawing Sheets

SYSTEM AND METHOD FOR MEDICAL INSTRUMENT STERILIZATION CASE HAVING A ROTATABLY DISPLACING COVER

CROSS REFERENCE TO RELATED APPLICATION

This application claims benefit of U.S. Provisional Application Ser. No. 61/166,348 filed Apr. 3, 2009, the entire disclosure of which is incorporated herein by reference.

FIELD OF THE DISCLOSURE

The present disclosure is generally related to sterilization cases and more particularly is related to sterilization cases having a rotatably displacing cover.

BACKGROUND OF THE DISCLOSURE

Sterilization cases are used in the medical field to hold medical instruments. The medical instruments, when contaminated, are run through a sterilizer while held within a sterilization case. Sterilization cases are frequently used in settings where space is limited and compact and easy-to-use items come in handy. In this regard, sterilization cases with easy-to-use parts may be desired to heighten the efficiency of sterilizing medical instruments. In addition, it is a frequent occurrence for parts of sterilization cases, such as covers, to become separated from the cases when they're opened, resulting in the eventual disappearance of the part. This may render the sterilization case less effective, and may make the overall sterilization process less efficient.

Thus, a heretofore unaddressed need exists in the industry to address the aforementioned deficiencies and inadequacies.

SUMMARY OF THE DISCLOSURE

Embodiments of the present disclosure provide a system and method for utilizing a medical instrument sterilization system. Briefly described, in architecture, one embodiment of the system, among others, can be implemented as follows. The medical instrument sterilization container includes a rotatably displacing cover. A rotatable device is integral with the cover. An elongate slot is formed in a side of the container for receiving the rotatable device, wherein the rotatable device is slidable within the elongate slot.

The present disclosure can also be viewed as providing a method of opening a medical instrument sterilization container. In this regard, one embodiment of such a method, among others, can be broadly summarized by the following steps: rotating a cover about an axis between a closed position and an open position using at least one rotatable device integral with the cover; and sliding the at least one rotatable device from a first position to a second position within an elongate slot formed in a side of the container, wherein the rotatable device is restricted to slide within the elongate slot.

The present disclosure can also be viewed as providing a method of manufacturing a medical instrument sterilization container having a plurality of sides and a cover. In this regard, one embodiment of such a method, among others, can be broadly summarized by the following steps: affixing a rotatable device to the cover; and securing the rotatable device within an elongate slot, wherein the elongate slot is disposed in a side of the container.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
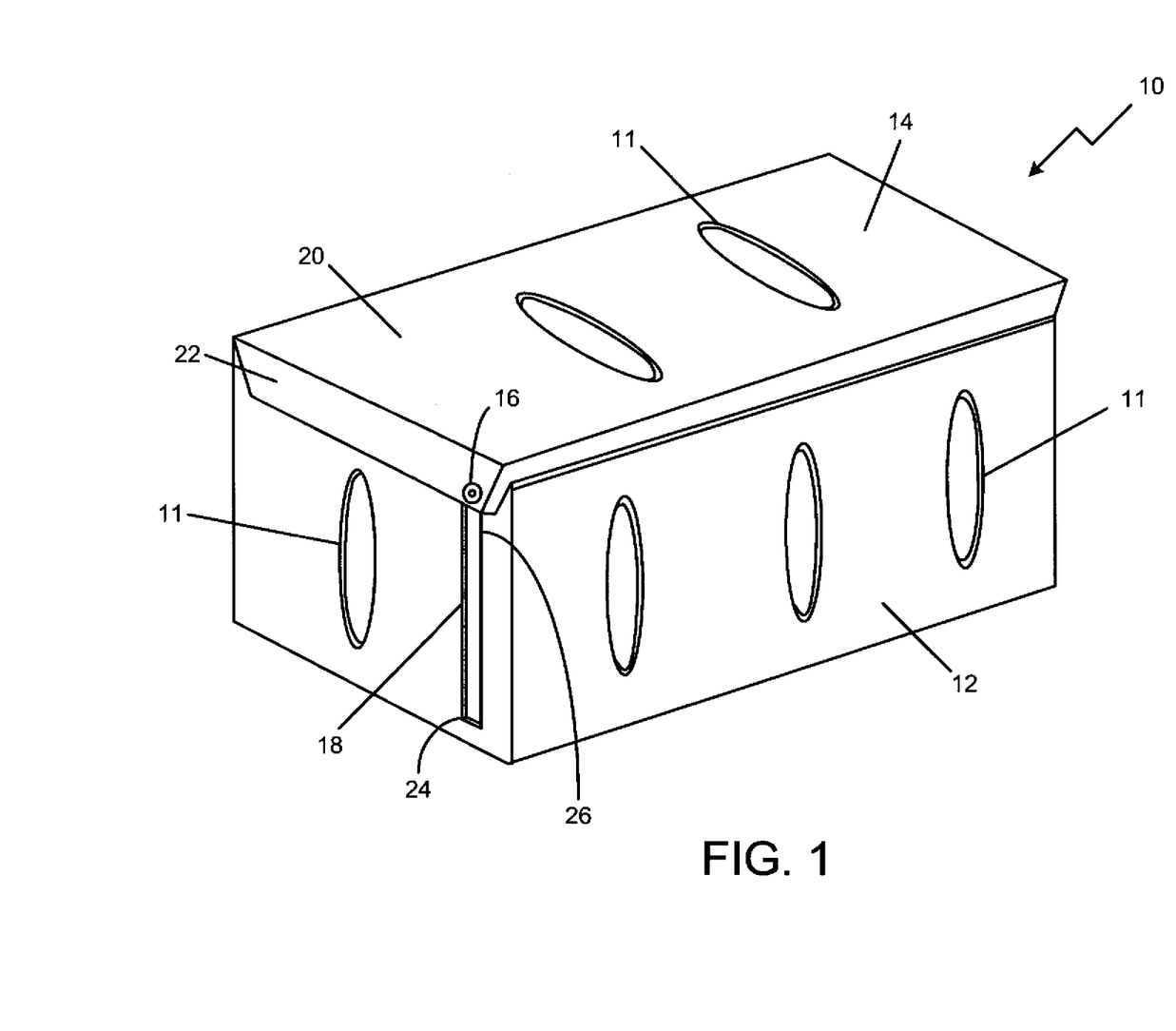
FIG. 1 is a perspective illustration of a medical instrument sterilization system, in accordance with a first exemplary embodiment of the present disclosure.

FIG. 1 is a perspective illustration of a medical instrument sterilization system 10, in accordance with a first exemplary embodiment of the present disclosure. In accordance with the first exemplary embodiment, the medical instrument sterilization system 10 includes a substantially enclosable structure capable of containing medical instruments during a sterilization process. The system 10 includes a plurality of openings 11 to allow sterilization material, such as water, steam, or another well-known sterilization material to penetrate through the system 10 and sterilize the instruments contained inside.

Generally, the system 10 contains a plurality of walls 12 connected to one another, and a cover 14, which may act as a side of the container. The cover 14 includes a planar surface 20 which may contain one or more openings 11 to permit the entry of sterilization material to an interior portion of the system 10. The cover 14 may further include a lip 22 located at one or more sides of the cover 14. Generally, the cover 14 will include a plurality of lips 22, which may assist with keeping the cover 14 located in the proper position. The cover 14 also includes a rotatable device 16 integral with the cover 14. Although the rotatable device 16 is integral with the cover 14, a rotatable device 16 that is removable and/or replaceable from the system 10 is considered within the scope of the present disclosure. In the first exemplary embodiment, the rotatable device 16 is located on the lip 22 of the cover 14, in a position proximate to an upper portion of the wall 12. However, the rotatable device may be located at another position on the lip 22 or the cover 14 without deviating from the scope of the present disclosure.

One or more of the walls 12, may include an elongate slot 18 formed within the wall 12. The elongate slot 18 may be formed at one edge of the wall 12 and may include a first end 24 and a second end 26. The elongate slot 18 is situated to receive the rotatable device 16, which may be moved between a position proximate to the first end 24 and a position proximate to the second end 26 of the elongate slot 18. In this arrangement, the elongate slot 18 will generally have a length measurement that is substantially greater than a width measurement. However, the elongate slot 18 may be located at any position within the wall 12 and include other dimensions as varied by design, all of which are considered within the scope of the present disclosure.

Figure 2:
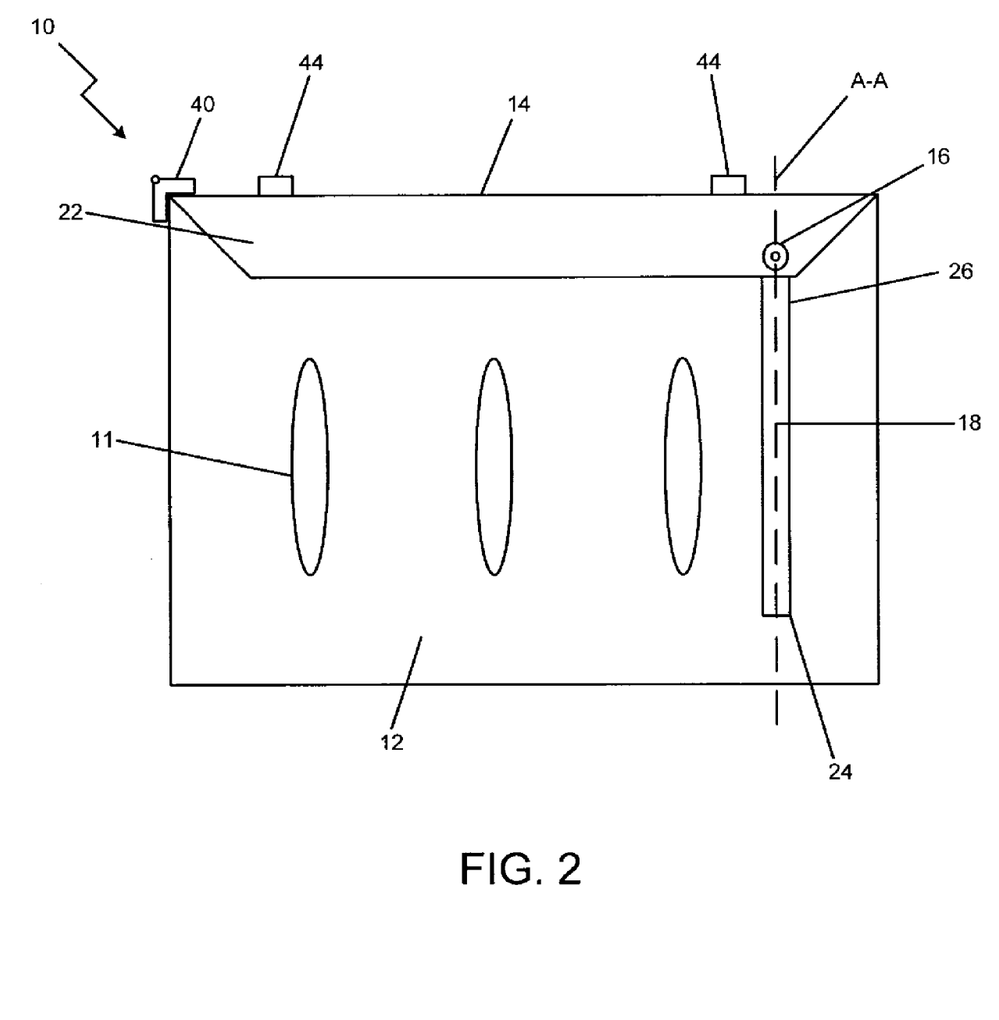
FIG. 2 is a side view of the medical instrument sterilization system shown in FIG. 1, in accordance with the first exemplary embodiment of the present disclosure.
Figure 3:
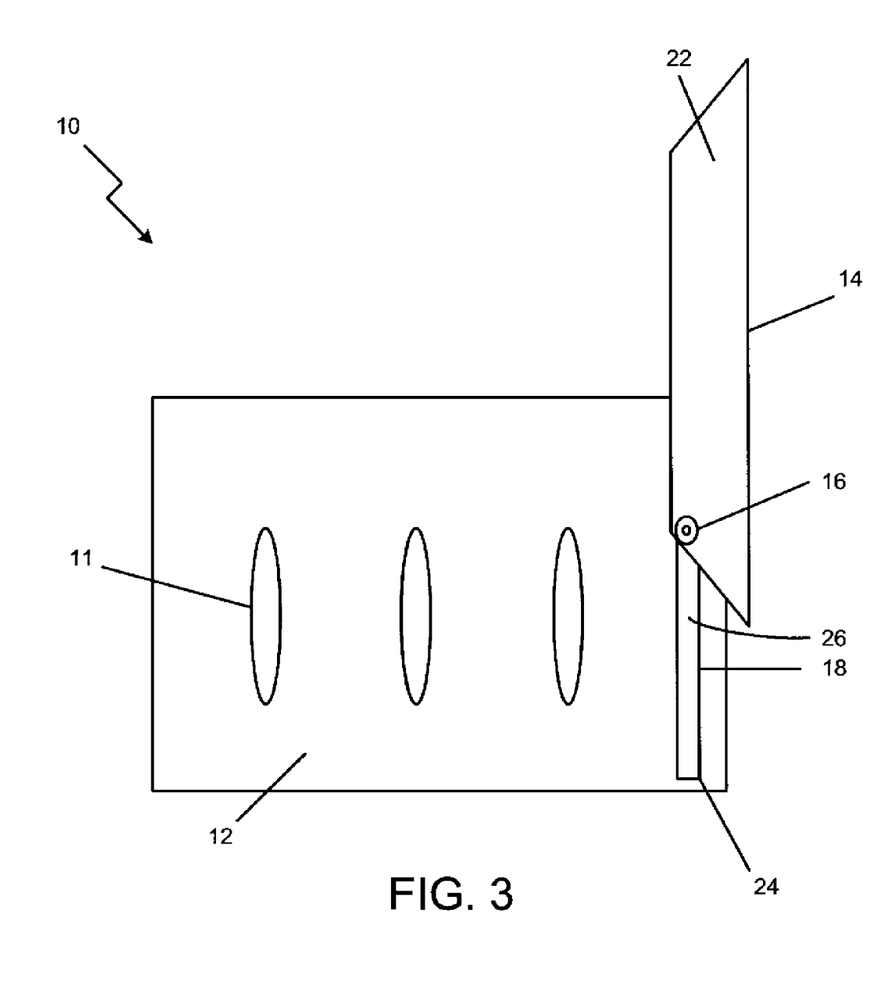
FIG. 3 is a side view of the medical instrument sterilization system shown in FIG. 1, in accordance with the first exemplary embodiment of the present disclosure, wherein the cover is in an open position.
Figure 4:
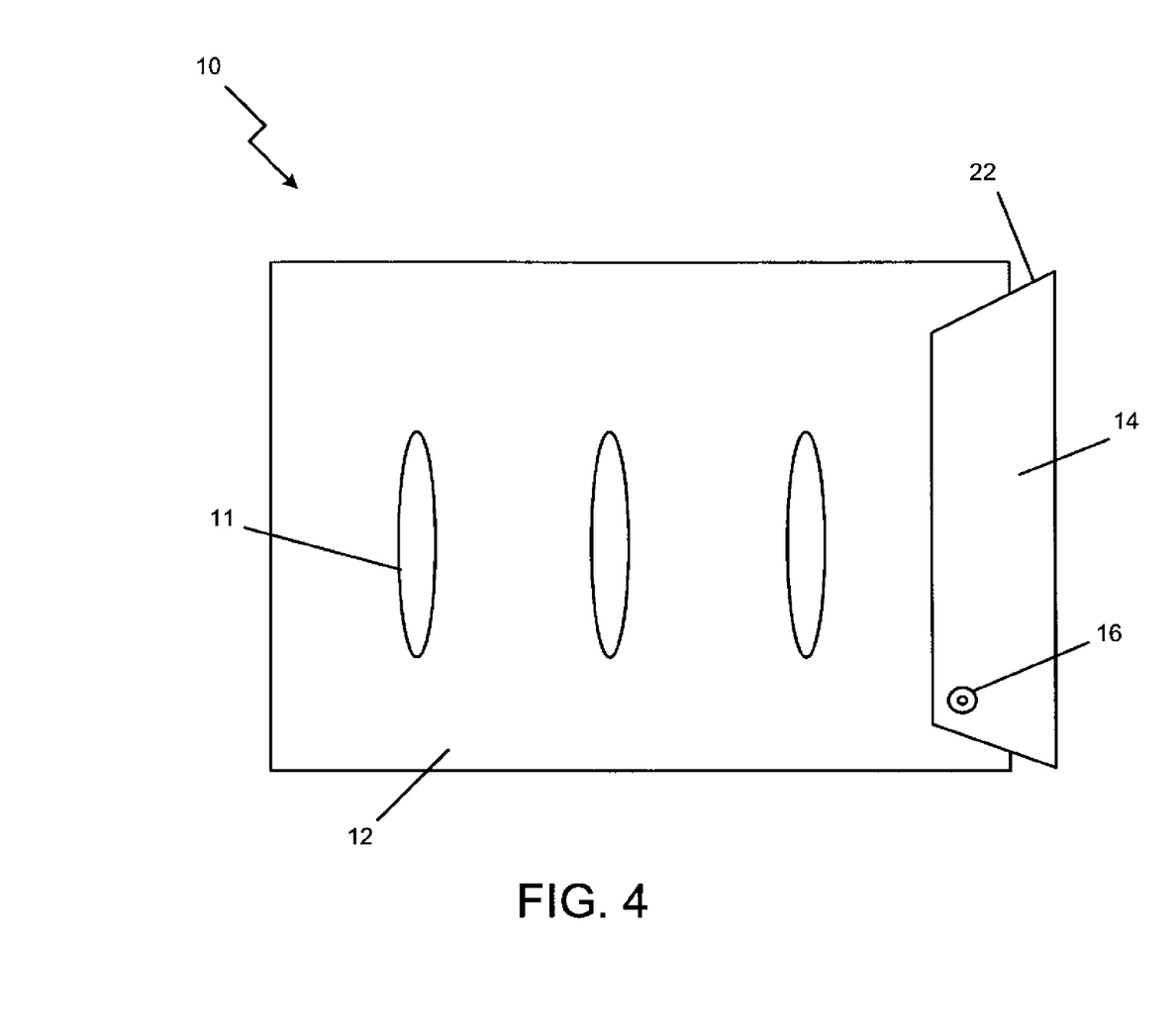
FIG. 4 is a side view of the medical instrument sterilization system shown in FIG. 1, in accordance with the first exemplary embodiment of the present disclosure, wherein the cover is in a retractable position.

FIGS. 2, 3 and 4 illustrate three side views of the medical instrument sterilization system 10 of FIG. 1, in accordance with the first exemplary embodiment of the present disclosure, with the cover 14 in three different positions. The three different positions of the cover 14 can be characterized as a closed position, shown in FIG. 2, an opened position, shown in FIG. 3, and a retracted position, shown in FIG. 4. In the closed position shown in FIG. 2, the cover 14 may be considered one side of the container, as the cover 14 encloses one side of the container. In another arrangement, the system 10 may further include a removable top wall positioned proximate to the cover 14, and interior of the cover 14, such that the top wall and the cover 14 enclose the system 10 together. In this arrangement, when the cover 14 is moved from the closed position to an open position, the top wall proximate to the cover 14 will remain in a position that encloses the system 10. This arrangement may allow the cover 14 to be opened while the system 10 remains enclosed.

The cover 14 may be affixed to the wall 12 by a rotatable device 16, which is disposed within an elongate slot 18 located within the wall 12. When the cover 14 is in the closed position, as shown in FIG. 2, the cover 14 is prevented from being displaced or removed, with the exception that it is capable of being rotated about an axis that is parallel with the rotation of the rotatable device 16. When the cover 14 is rotated about the rotatable device 16, the cover may be lowered into the retracted position (FIG. 4) with the rotatable device 16 traversing along the line A-A. Although the elongate slot 18 and the line A-A are illustrated as substantially linear, the elongate slot 18 may include any shape, such as an arc with a curvature. The system 10 may also include locking mechanism 40 to retain the cover 14 in the closed position, thereby preventing unintentional movement of the cover 14. The locking mechanism 40 may include any type of device, such as a fastener or a structural lock, located proximate to the cover 14 or any other component of the system 10. All configurations and variations are considered within the scope of the present disclosure.

FIG. 3 shows the system 10 with the cover 14 in the opened position. In use, starting from the closed position of FIG. 2, the opened position may be achieved by rotating the cover 14 about the axis parallel with the rotation of the rotatable device 16. The opened position may be characterized by a measurement of rotation about the axis, and may include any rotation greater than 0 degrees. In other words, the open position may include a position where the cover 14 is only slightly rotated, or when the cover 14 has been rotated 90 degrees or more, or any position in between. For example, in FIG. 3, the opened position is illustrated with the cover 14 at a rotation measurement of approximately 90 degrees, thereby exposing the wall 12 of the container that was previously covered by the cover 14. As one having skill in the art would understand, rotation of the cover 14 to the open position may allow the interior portion of the container to be accessible. Varying designs may include a cover 14 that can be rotated more than 90 degrees, such as 180 degrees. In the opened position shown in FIG. 3, it can be seen that the rotatable device 16 integral with the cover 14 is positioned to slide from the second end 26 of the elongate slot 18, to the first end 24.

FIG. 4 shows the system 10 with the cover 14 in a retracted position. In use, starting from the opened position of FIG. 3, the retracted position is achieved by sliding the rotatable device 16 from a first position to a second position (along line A-A of FIG. 2; 26, 24 of FIG. 3) within the elongate slot 18. As is understood from FIGS. 3 and 4, a movement of the rotatable device 16 translates into movement of the cover 14, thereby positioning the cover 14 proximate to a wall 12 of the system 10. Generally, the wall 12 will be proximate to the cover 14, when the cover 14 is in the retracted position. When the cover 14 is in the closed position (FIG. 2), the cover 14 will be perpendicular to the wall 12 located on the side of the container. However, varying designs may include a retracted position proximate to any wall 12 of the system 10, or any other feature of the system 10.

In accordance with the first exemplary embodiment of the present disclosure, the system 10 may include features to allow a plurality of systems 10 to be stacked, regardless of the position of the cover 14. This may include features that are integral with any component of the system 10, such as interconnecting structures 44, as is depicted in FIG. 2. Additionally, other features may be included with the system 10, such as a retaining mechanism (not shown) that may prevent rotation of the cover 14 when it is in the retracted position. This retaining mechanism may assist with keeping the cover 14 from lifting away from the system 10 and contacting an object proximate to the system 10.

Figure 5:
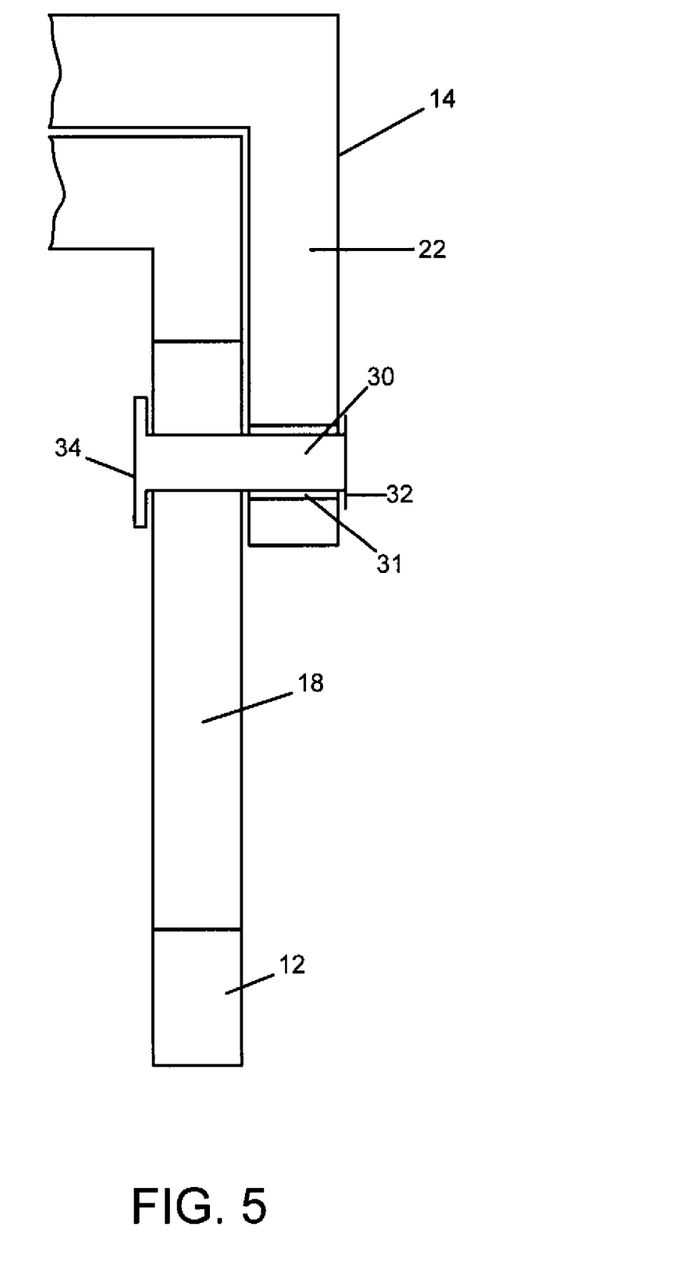
FIG. 5 is a cross-sectional illustration of the rotatable device and the elongate slot of the medical instrument sterilization system shown in FIG. 1, in accordance with the first exemplary embodiment of the present disclosure.

FIG. 5 is a cross-sectional illustration, taken along the line A-A of FIG. 2, of the rotatable device 16 and the elongate slot 18 of the medical instrument sterilization system 10 of the first exemplary embodiment. The rotatable device 16 may include any device capable of affixing the cover 14 to a wall 12 and allowing the cover 14 to rotate about an axis parallel with the rotation of the rotatable device 16. One example of a rotatable device 16 includes a pin and hole system, as is shown in FIG. 5. However, other examples of a rotatable device may include a shaft and bearing system, an interconnecting system, or a male and female connector system. A variety of other rotatable devices 16 may be used without deviating from the scope of the present disclosure.

In accordance with the first exemplary embodiment of the present disclosure, the rotatable device 16 shown in FIG. 5 includes a pin 30 affixing the cover 14 to the wall 12. The cover 14 may include a hole 31 for receiving the pin 30. The pin 30 may include a front stop 32 and a back stop 34, preventing the pin 30 from slipping or being moved unintentionally from within the hole 31. The front stop 32 may be a cotter pin or any other device commonly known for preventing movement of the pin 30. The back stop 34 may include a variety of devices, including an integral lip on the pin 30, as is shown in FIG. 5. In one of many alternative arrangements, the back stop 34 may include a separate structure affixed to the pin 30, such as a threaded fastener. The system 10 may also include any number of additional features, such as a washer proximate to the pin 30, a lubricant proximate to the hole 31, or a retention device restricting movement of the pin 30. As is shown in FIG. 5, the pin 30 is positioned within the hole 31 of the cover 14 and the elongate slot 18, such that the cover 14 and the wall 12 are located between the front stop 32 and the back stop 34. This arrangement may allow the rotatable device 16 to slide along the elongate slot 18 and move the cover 14 between the open position and the retracted position, 24, 26 (discussed with respect to FIG. 3).

Figure 6:
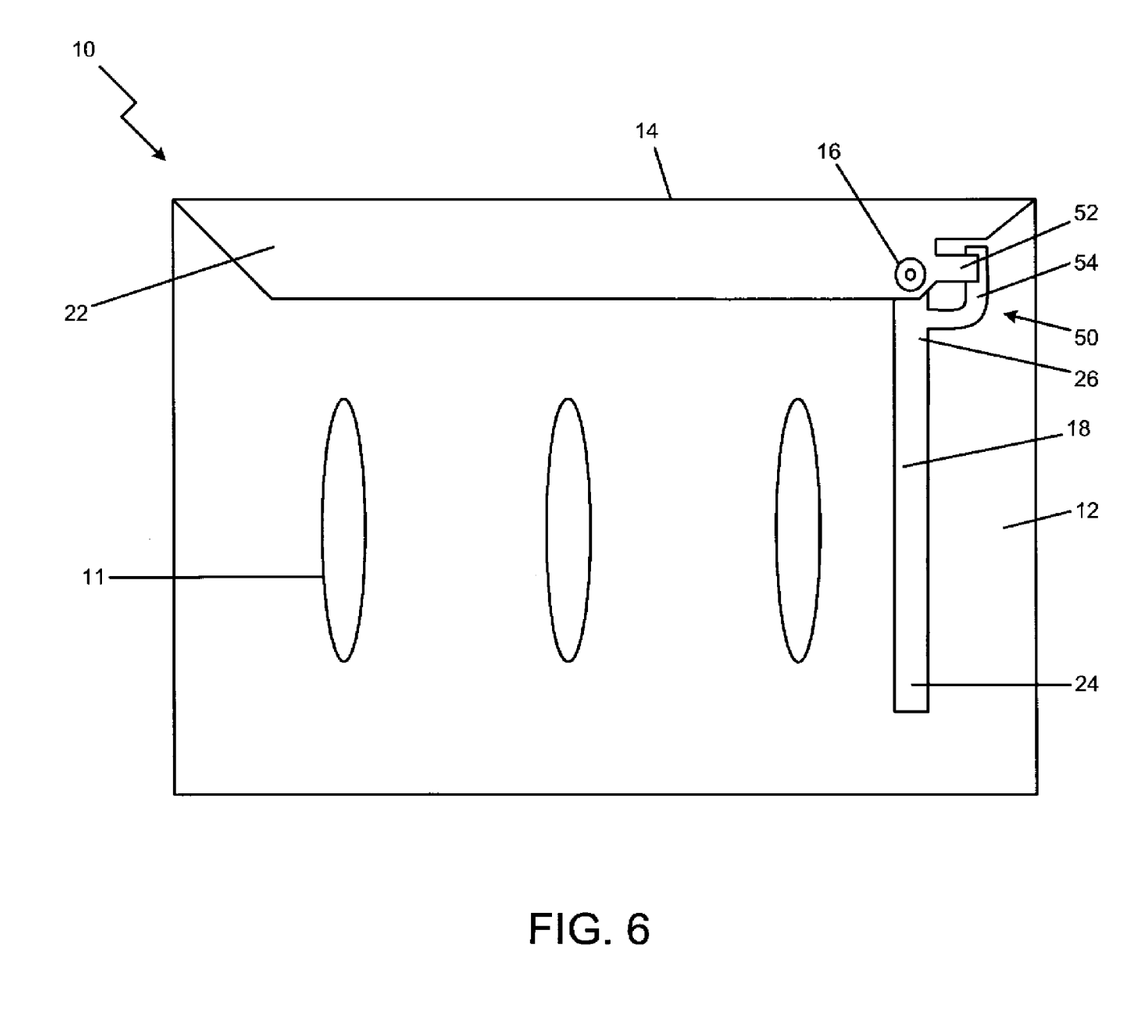
FIG. 6 is a side view illustrating a guiding device of the medical instrument sterilization system shown in FIG. 1, in accordance with the first exemplary embodiment of the present disclosure.
Figure 6A:
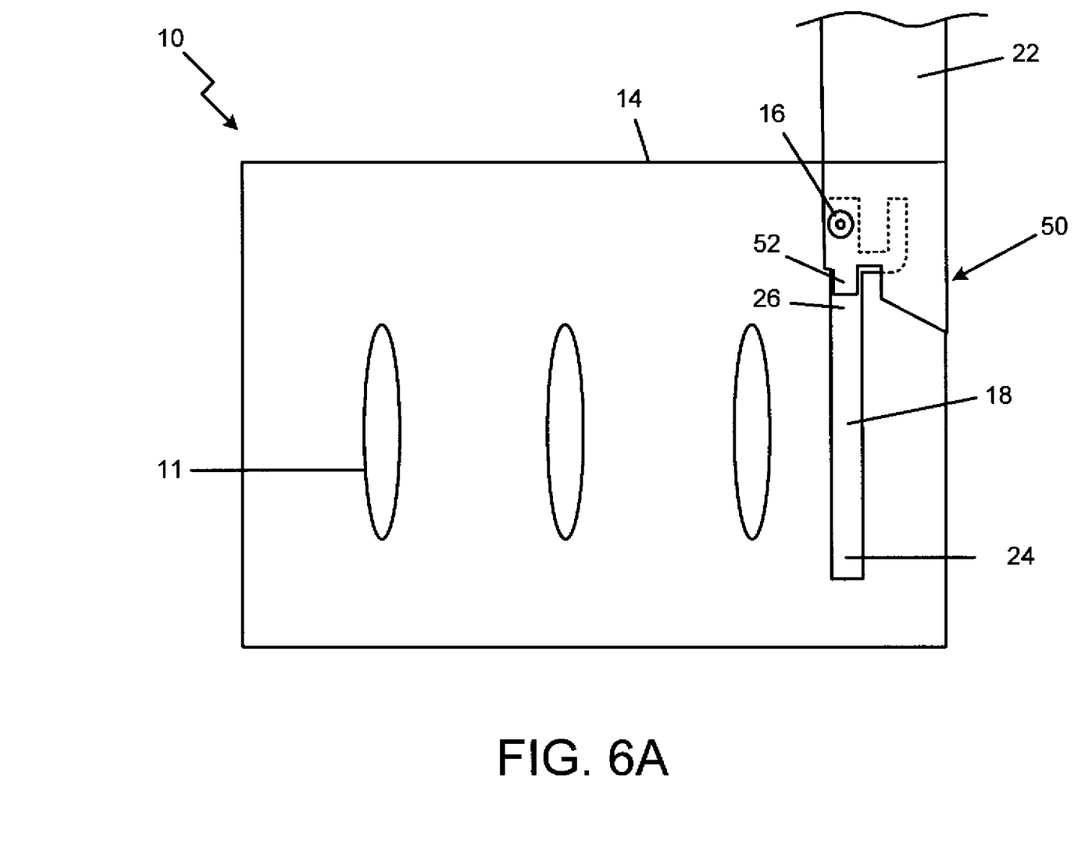
FIG. 6A is a side view illustrating a guiding device of the medical instrument sterilization system shown in FIG. 1, in accordance with the first exemplary embodiment of the present disclosure.

FIG. 6 and FIG. 6A are a side view illustrating a guiding device 50 of the medical instrument sterilization system 10 of the first exemplary embodiment. The guiding device 50 includes a guide arm 52 and a receiving slot 54. The guide arm 52 may be integral, attached, or removably attached with the rotatable device 16 or the cover 14. The guide arm 52 includes an end portion situated to be received by the receiving slot 54. In accordance with the first exemplary embodiment, the end portion of the guide arm 52 may include an angled or bent design that penetrates an outer plane of the container. However, other features may be included with guide arm 52 in accordance with varying designs, and are considered within the scope of the present disclosure.

In use, the guiding device 50 guides the cover 14 as it is moved from a closed position to an open position, and vice versa. The guiding device 50 may also prevent the cover 14 from sliding within the elongate slot 18 until the cover 14 is in a desired position. In FIG. 6, the desired position is illustrated as approximately 90 degrees, and when the cover 14 is in a 90 degree open position, the guide arm 52 of the guiding device 50 will exit the receiving slot 54 and be located parallel to the length of the elongate slot 18. In this arrangement, the rotatable device 16 may be moved from a first position 26 along the elongate slot 18 to a second position 24, allowing the cover 14 to be moved into the retracted position.

Figure 7:
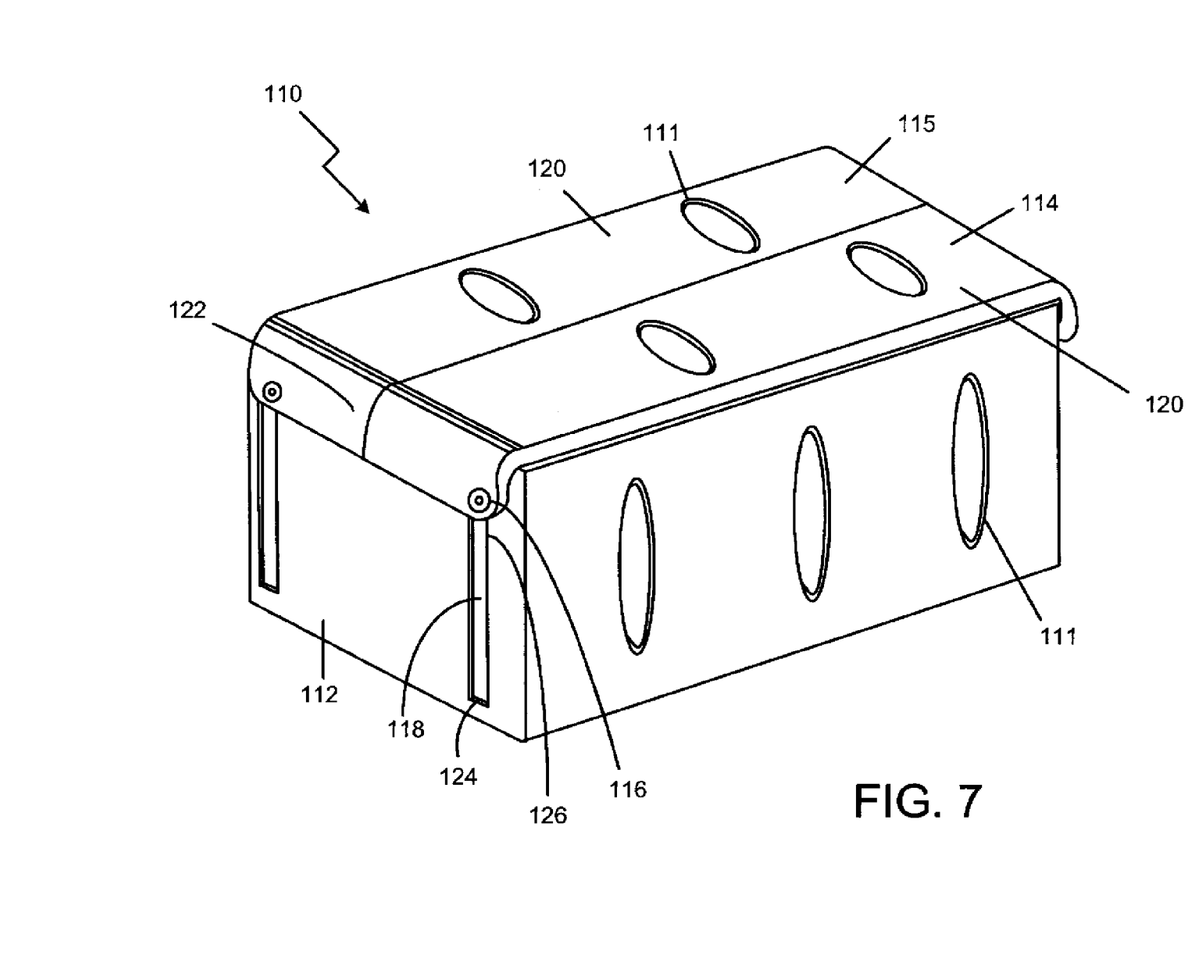
FIG. 7 is a perspective illustration of a medical instrument sterilization system, in accordance with a second exemplary embodiment of the present disclosure.

FIG. 7 is a perspective illustration of a medical instrument sterilization system 110, in accordance with a second exemplary embodiment of the present disclosure. The system 110 of the second exemplary embodiment is similar from the system 10 of the first exemplary embodiment. However, the system 110 differs in that it includes a first cover 114 and a second cover 115 that may be rotated about a second axis between a closed position and an open position using a second rotatable device 116 integral with the second cover 115. In accordance with this embodiment, the rotatable device 116 may be situated to slide between a first position and a second position within an elongate slot 118, which is formed within a wall 112 of the system 110.

Generally, the system 110 contains a plurality of walls 112 connected to one another, a first cover 114, and a second cover 115. The first and second covers 114, 115 may act as one side of the system 110. The first and second covers 114, 115 include planar surfaces 120 which may contain one or more openings 111 to permit the entry of sterilization material to an interior portion of the system 110. The first and second covers 114, 115 may further include a lip 122 located at one or more sides of the covers. Generally, the first and second covers 114, 115 will include a plurality of lips 122, which may assist with retaining the covers 114, 115 in specific positions. The first and second covers 114, 115 also each include rotatable devices 116 integral with the covers 114, 115. Although the rotatable devices 116 are integral with the first and second covers 114, 115, a rotatable device 116 that is removable and/or replaceable is considered within the scope of the present disclosure. Similar to the first exemplary embodiment, the rotatable device 116 of the second exemplary embodiment is located on the lip 122 of the first and second covers 114, 115, in a position proximate to an upper portion of the wall 112. However, the rotatable device 116 may be located at another position on the lip 122 or the first and second covers 114, 115 without deviating from the scope of the present disclosure.

One or more of the walls 112, may include an elongate slot 118. As shown in FIG. 7, there are two elongate slots 118 for use with the first and second covers 114, 115 on the illustrated side of the system 110. The elongate slots 118 may be formed at an edge of the wall 112 and may include a first end 124 and a second end 126. The elongate slots 118 are situated to receive the rotatable devices 116, and allow the rotatable devices 116 to move between a position proximate to the first end 124 and a position proximate to the second end 126. In this arrangement, the elongate slots 118 may have a length measurement that is substantially greater than a width measurement. However, the elongate slots 118 may be located on any portion of the container and may include any other dimensions as varied by design. All configurations and designs are considered with the scope of the present disclosure.

In use, the first and second covers 114, 115 of the second exemplary embodiment operate in a similar manner to the cover 14 of the first exemplary embodiment. Both of the first and second covers 114, 115 may be situated in three different positions, characterized as a closed position, an open position, and a retracted position, similar to FIGS. 2, 3 and 4 of the first embodiment. In the closed position, the first and second covers 114, 115 may be considered one side of the container, as the covers 114, 115 enclose the container. In another arrangement, the system 110 may include a wall 112 positioned proximate to the covers 114, 115, and to the interior thereof, such that the wall 112 and the covers 114, 115 enclose the system 110 together. In this arrangement, when the covers 114, 115 are moved from the closed position to the open position, the wall 112 proximate to the covers 114, 115 will remain in a position that encloses the system 110.

The covers 114, 115 are affixed to the wall 112 by the rotatable devices 116, which are disposed within the elongate slots 118 located within the wall 112. When the covers 114, 115 are in the closed position, they are prevented from being displaced or removed, except for being rotated, as described below. The system 110 may also include a locking mechanism (shown in FIG. 2) to retain the covers 114, 115 in the closed position, thereby preventing unintentional movement of the first and second covers 114, 115.

In use, when moving the first and second covers 114, 115 from the closed position to the opened position, the covers 114, 115 may be rotated about the axes parallel with the rotation of the rotatable devices 116, respectively. The opened position may be characterized by a measurement of rotation about the axis, including a rotation greater than 0 degrees, i.e., when the covers 114, 115 are only slightly rotated or slightly opened. In the opened position, the rotatable devices 116 are positioned to slide from the second end 126 of the elongate slots 118, to the first end 124. When the rotatable devices 116 are positioned at the first end 124, the position of the covers 114, 115 may be characterized as being in a retracted position. In this arrangement, the covers 114, 115 will be in a position proximate to a wall 112 of the system 110. Generally, the wall 112 will be proximate to the covers 114, 115, when the covers 114, 115 are in the retracted position. When the covers 114, 115 are in the closed position, they will be perpendicular to the wall 112 on the side of the container. However, varying designs may include a retracted position proximate to any wall 112 of the system 110, or any other feature of the system 110.

In accordance with the second exemplary embodiment of the present disclosure, the system 110 may include features to allow a plurality of systems 110 to be stacked, regardless of the position of the first and second covers 114, 115. Additionally, other features may be included with the system 110, such as a retaining mechanism (not shown) that may prevent rotation of the covers 114, 115 when they are in the retracted position. A guide system (not shown) as described with respect to the first exemplary embodiment may also be included with the second exemplary embodiment. Furthermore, the rotatable devices 116 may perform in the same manner as described with respect to the first exemplary embodiment. Additionally, the first and second cover 114, 115 of the system 110 may be moved independently of one another. For example, the first cover 114 may be moved to the open position while the second cover 115 remains stationary, and vice versa.

Figure 8:
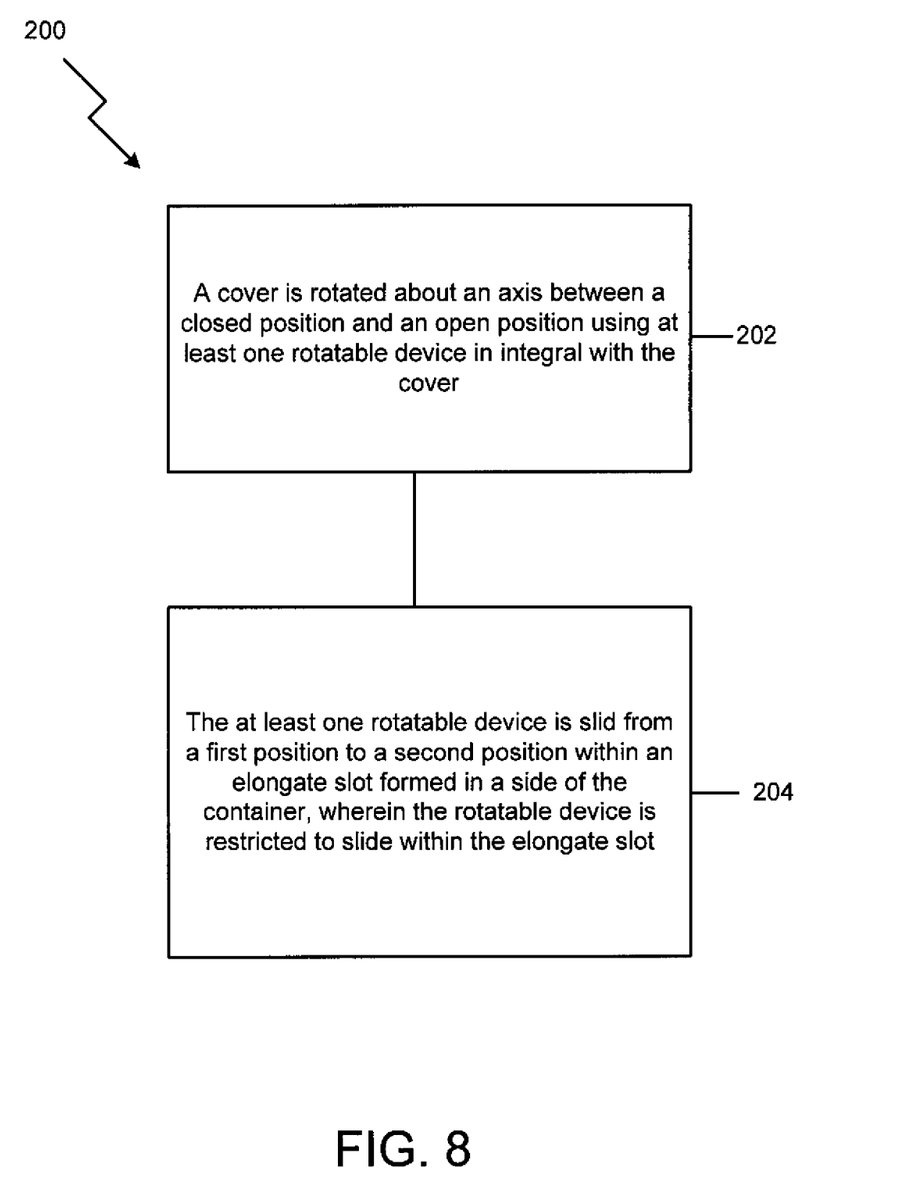
FIG. 8 is a flowchart illustrating a method of utilizing the medical instrument sterilization system of FIG. 1, in accordance with the first exemplary embodiment of the present disclosure.

FIG. 8 is a flowchart 200 illustrating a method of utilizing the medical instrument sterilization system of FIG. 1, in accordance with the first exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

At block 202, a cover is rotated about an axis between a closed position and an open position using at least one rotatable device in integral with the cover. At block 204, the at least one rotatable device is slid from a first position to a second position within an elongate slot formed in a side of the container, wherein the rotatable device is restricted to slide within the elongate slot.

The method of utilizing the medical instrument sterilization system may include any number of additional steps. A second cover may be included, wherein the second cover is rotated about a second axis between a closed position and an open position using at least one second rotatable device integral with the second cover. The at least one second rotatable device may be slid from a first position to a second position within a second elongate slot formed in a side of the container, wherein the second rotatable device is restricted to slide within the second elongate slot. The first and second covers may be rotated in combination with, or independent of each other, as will vary by design. Any movement of the first or second covers may be guided with a guiding device. The guiding device may prevent the first or second cover from sliding within the first or second elongate slot and may also allow the first or second cover to slide within the first or second elongate slot when the first or second cover, respectively, is located in a predetermined position. Movement of the first or second cover may be restricted with a locking mechanism.

Figure 9:
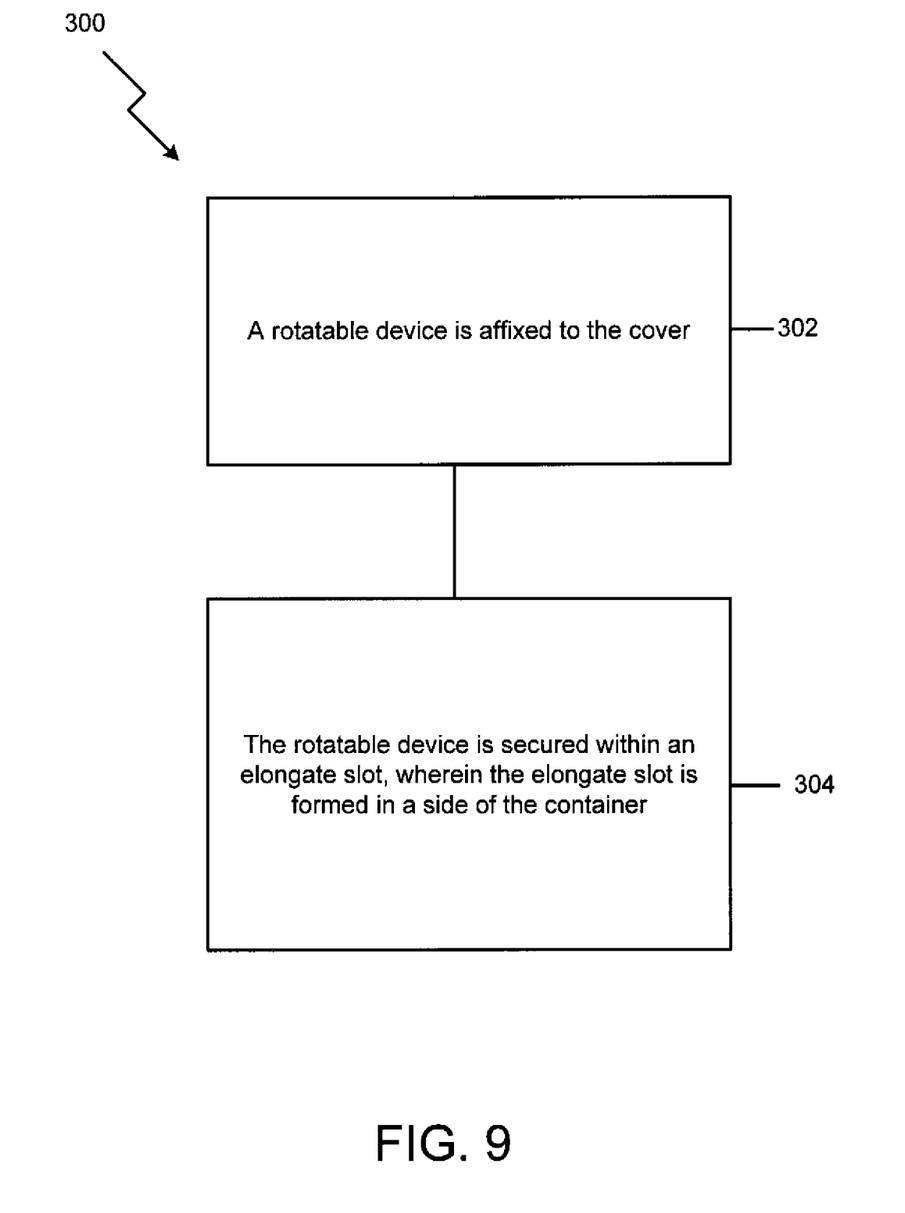
FIG. 9 is a flowchart illustrating a method of manufacturing a medical instrument sterilization container having a plurality of sides and a cover, in accordance with a third exemplary embodiment of the present disclosure.

FIG. 9 is a flowchart 300 illustrating a method of manufacturing a medical instrument sterilization container having a plurality of sides and a cover, in accordance with a third exemplary embodiment of the present disclosure. It should be noted that any process descriptions or blocks in flow charts should be understood as representing modules, segments, portions of code, or steps that include one or more instructions for implementing specific logical functions in the process, and alternate implementations are included within the scope of the present disclosure in which functions may be executed out of order from that shown or discussed, including substantially concurrently or in reverse order, depending on the functionality involved, as would be understood by those reasonably skilled in the art of the present disclosure.

At block 302, a rotatable device is affixed to the cover. The rotatable device is secured within an elongate slot, wherein the elongate slot is formed in a side of the container (block 304). The method of manufacturing a medical instrument sterilization container having a plurality of sides and a cover may include any number of additional steps. A plurality of rotatable devices may be affixed to a plurality of covers. The plurality of rotatable devices may be secured within a plurality of elongate slots.

It should be emphasized that the above-described embodiments of the present disclosure, particularly, any "preferred" embodiments, are merely possible examples of implementations, merely set forth for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure and the present disclosure and protected by the following claims.

What is claimed is:

1. A method of opening a medical instrument sterilization container, the method comprising the steps of:

rotating a first cover about an axis between a closed position and an open position using at least one rotatable device integral with the first cover;

sliding the at least one rotatable device from a first position to a second position within a first elongate slot formed in a first side of the container, wherein a length of the first elongate slot is positioned substantially perpendicular to a top planar surface of the first cover in the closed position, and wherein the rotatable device is restricted to slide within the first elongate slot;

guiding the first cover between the closed and open positions with at least one guide arm, wherein the guide arm is integral with the first cover and positioned to engage with the first elongate slot and a guiding slot formed within the side of the container, the guiding slot having a first portion and a second portion, wherein the first portion is connected to the first elongate slot at a position between the first end and the second end of the first elongate slot, wherein a length of the first portion is positioned substantially perpendicular to the first elongate slot, and wherein the second portion is connected to the first portion, wherein a length of the second portion is positioned substantially parallel to the length of the first elongate slot, and wherein the first elongated slot and the second portion of the guiding slot have a common termination height along the container; and retracting the first cover into a retracted position, wherein when the first cover is in the retracted position, the rotatable device and the guide arm are positioned within the first elongated slot and the first cover is positioned exterior of the container and parallel to a second side of the container, wherein the second side of the container is substantially perpendicular to the first side.

2. The method of claim 1, further comprising the steps of:

rotating a second cover about a second axis between a closed position and an open position using at least one second rotatable device integral with the second cover; and sliding the at least one second rotatable device from a first position to a second position within a second elongate slot formed in a side of the container, wherein the second rotatable device is restricted to slide within the second elongate slot.

3. The method of claim 2, wherein the second cover is rotated independently of the first cover.

4. The method of claim 2, further comprising guiding the movement of the second cover with a second guide arm.

5. The method of claim 4, further comprising the steps of:

preventing the first cover from sliding within the first elongate slot with the guide arm; and allowing the first cover to slide within the first elongate slot when the first cover is located in a predetermined position, wherein the predetermined positioned further comprises a position where the first cover is positioned substantially parallel to the second side of the container.

6. The method of claim 2, further comprising restricting the movement of at least one of the first cover and the second cover with a locking mechanism.

7. A medical instrument sterilization container having a rotatably displacing cover comprising:

a first cover having at least a closed position, an open position, and a retracted position;

a rotatable device integral with the first cover;

a first elongate slot formed within a first side of the container for receiving the rotatable device, wherein a length of the first elongate slot is positioned substantially perpendicular to a top planar surface of the first cover in the closed position, and wherein the rotatable device is slidable within the first elongate slot;

a guiding slot formed within the side of the container, the guiding slot having a first portion and a second portion, wherein the first portion is connected to the first elongate slot at a position between the first end and the second end of the first elongate slot, wherein a length of the first portion is positioned substantially perpendicular to the first elongate slot, and wherein the second portion of the guiding slot is connected to the first portion, wherein a length of the second portion is positioned substantially parallel to the length of the first elongate slot, and wherein the first elongated slot and the second portion of the second slot have a common termination height along the container; and a guide arm integral with the first cover and positioned to engage with the first elongate slot and the first and second portions of the guiding slot, wherein when the first cover is in the retracted position, the rotatable device and the guide arm are positioned within the first elongated slot and the first cover is positioned exterior of the container and parallel to a second side of the container, wherein the second side of the container is substantially perpendicular to the first side.

8. The medical instrument sterilization container of claim 7, further comprising:

a second cover;

a second rotatable device integral with the second cover; and a second elongate slot formed within a side of the container for receiving the second rotatable device, wherein the second rotatable device is slidable within the second elongate slot.

9. The medical instrument sterilization container of claim 8, further comprising a second, wherein the second guide arm guides a movement of the second cover.

10. The medical instrument sterilization container of claim 8, wherein the guide arm engages at least a portion of the at least one of the first elongate slot and the second elongate slot.

11. The medical instrument sterilization container of claim 9, wherein the second guide arm engages with the second elongate slot when the second cover is in the closed position, and wherein the second guide arm moves along the length of the second elongate slot when the second first cover is in a retracted position.

12. The medical instrument sterilization container of claim 7, wherein the rotatable device is restricted from moving within the first elongate slot.

13. The medical instrument sterilization container of claim 7, further comprising a locking mechanism positioned to restrict movement of the first cover.

14. The medical instrument sterilization container of claim 7, further comprising:

a plurality of rotatable devices affixed to the first cover; and a plurality of elongate slots within one or more sides of the container for receiving the plurality of rotatable devices.

15. The medical instrument sterilization container of claim 7, further comprising a stacking device for stacking a plurality of medical instrument sterilization containers.

16. The medical instrument sterilization container of claim 7, wherein the rotatable device received in the first elongate slot is removable.

17. A method of manufacturing a medical instrument sterilization container having a plurality of sides and a cover, the method comprising:

affixing a rotatable device to the cover, wherein the cover has at least a closed position and an open position;

securing the rotatable device within an elongate slot, wherein the elongate slot is formed in a first side of the container, and wherein a length of the elongate slot is positioned substantially perpendicular to a top planar surface of first cover in the closed position; and affixing a guide arm integral with the first cover, wherein the guide arm is positioned to engage with the elongate slot and a slot formed within the side of the container, the guiding slot having a first portion and a second portion, wherein the first portion is connected to the first elongate slot at a position between the first end and the second end of the first elongate slot, wherein a length of the first portion is positioned substantially perpendicular to the first elongate slot, and wherein the second portion is connected to the first portion, wherein a length of the second portion is positioned substantially parallel to the length of the first elongate slot, and wherein the first elongated slot and the second portion of the guiding slot have a common termination height along the container; and retracting the first cover into a retracted position, wherein when the first cover is in the retracted position, the rotatable device and the guide arm are positioned within the first elongated slot and the first cover is positioned exterior of the container and parallel to a second side of the container, wherein the second side of the container is substantially perpendicular to the first side.

18. The method of claim 17 further comprising:
affixing a plurality of rotatable devices to a plurality of covers; and
securing the plurality of rotatable devices within a plurality of elongate slots.

* * * * *

UNITED STATES PATENT AND TRADEMARK OFFICE
CERTIFICATE OF CORRECTION

PATENT NO. : 8,511,510 B2
APPLICATION NO. : 12/753500
DATED : August 20, 2013
INVENTOR(S) : David R. Pratte and Michael Sullivan

Page 1 of 1

It is certified that error appears in the above-identified patent and that said Letters Patent is hereby corrected as shown below:

In the Claims

Column 10, Claim 11, Line 19, after "second" remove "first".
Column 10, Claim 17, Line 50, add "guiding" between "a" and "slot".

Signed and Sealed this
Twenty-third Day of September, 2014

Michelle K. Lee
*Deputy Director of the United States Patent and Trademark Office*